United States Patent
Ozaki et al.

(10) Patent No.: US 6,900,052 B1
(45) Date of Patent: May 31, 2005

(54) METHOD OF CULTURING CELLS

(75) Inventors: Yasuko Ozaki, Gotemba (JP); Yasuo Koishihara, Gotemba (JP); Shin-ichi Kaiho, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/959,348

(22) PCT Filed: May 10, 2000

(86) PCT No.: PCT/JP00/02997

§ 371 (c)(1),
(2), (4) Date: Oct. 23, 2001

(87) PCT Pub. No.: WO00/68371

PCT Pub. Date: Nov. 16, 2000

(30) Foreign Application Priority Data

May 10, 1999 (JP) .......................................... 11/128614

(51) Int. Cl.$^7$ ............................. C12N 5/00; C12N 5/02; C12N 5/06
(52) U.S. Cl. ....................... 435/373; 435/325; 435/326; 435/346; 435/347; 435/252.3; 435/254.11
(58) Field of Search ................................ 435/373, 325, 435/326, 254.11, 254.2, 252.3, 346, 347, 358

(56) References Cited

U.S. PATENT DOCUMENTS 5,585,089 A * 12/1996 Queen et al. ............. 424/133.1

FOREIGN PATENT DOCUMENTS

| EP | 0 854 152 A1 | | 7/1998 |
|---|---|---|---|
| GB | 2 232 998 | | 1/1991 |
| WO | WO 91/03553 | * | 3/1991 |
| WO | WO 93/07281 | | 4/1993 |
| WO | WO 98/13388 | | 4/1998 |
| WO | WO 98/14580 | | 4/1998 |

OTHER PUBLICATIONS

Mikayama et al. Proc. Natl. Acad. Sci. USA, vol. 90, pp. 10056–10060, 1993.*
Kao et al. "Genetics of Somatic Mammalian Cells, VII. Induction and Isolation of Nutritional Mutants in Chinese Hamster Cells" Proc. Natl. Acad. Sci. USA vol. 60, pp. 1275–1281, 1968.
Urlaub "Deletion of the Diploid Dihydrofolate Reductase Locus from Cultured Mammalian Cells" Cell, vol. 33, 405–412, Jun. 1983.
Urlaub et al. "Isolation of Chinese Hamster Cell Mutants Deficient in Dihydrofolate Reductase Activity" Proc. Natl. Acad. Sci. USA vol. 77, No. 7, pp. 4216–4220, Jul. 1980.
Sambrook, et al. "Transfection of Corpecipitase of Calcium Phosphate and DNA" Expression of Cloned Genes in Cultured Mammalian Cells, pp. 16.32–16.36, 1989.
Kudo, et al. "A Simple and Improved Method to Generate Human Hybridomas" Journal of Immunological Methods, 145(1991) pp. 119–125.

* cited by examiner

*Primary Examiner*—Prema Mertz
(74) *Attorney, Agent, or Firm*—Morrison & Foerster LLP

(57) ABSTRACT

A method of culturing a protein-producing cell, said method comprising co-culturing one transformed cell that can constitutively produce said protein with the parent cell of said transformed cell.

13 Claims, No Drawings

METHOD OF CULTURING CELLS

TECHNICAL FIELD

The present invention relates to a method of culturing cells. The present invention also relates to a method of screening cells. Furthermore, the present invention relates to a method of producing a protein by cell culture.

BACKGROUND ART

A cell group grown from a single cell is thought to be composed of cells each having entirely identical traits, and single cell cloning to obtain such a homogeneous cell group has become an important technology both academically and commercially. For example, in order to manufacture pharmaceuticals for which preparation of homogeneous products is a prerequisite, especially for the manufacture of a protein, it is necessary to select, isolate, and grow a single cell that produces said protein and thereby to construct homogeneous cells groups that produce said protein. Single cell cloning has, therefore, become an indispensable technology for the production of proteins, in particular recombinant proteins.

The conventional method of preparing a monoclonal antibody that requires single cell cloning has employed the so-called limiting dilution method in which spleen cells obtained from an animal immunized with an antigen and immortalized myeloma cells were subjected to cell fusion to prepare hybridomas, and each cell of the heterogeneous cell group thus prepared was cultured together with a feeder cell. As the feeder cells, at this time, spleen cells that were subjected to mitomycin or radiation treatment, in order to deprive the cells of the ability to grow, have been used.

In cases where culturing was difficult, a growth factor such as IL-6 was further added to the culture system. However, these methods had the disadvantages that the feeder cells used were not a homogeneous cell group, variation due to experimental procedures was large, pretreatment to incapacitate the growth ability was required, and the like. Furthermore, in some cells, growth from single cells was difficult even if the feeder cell was added or a growth factor and fetal bovine serum were added.

DISCLOSURE OF THE INVENTION

The present invention provides a method of culturing one cell or a method of cloning cells and, at the same time, provides a method of obtaining a protein by cell culture, said method having none of the disadvantages found in the conventional limiting dilution method.

After intensive study, the inventors of the present invention have found that a homogeneous cell group can be efficiently constructed by co-culturing one transformed cell or one hybridoma cell producing protein with the parent cell.

EMBODIMENTS FOR CARRYING OUT THE INVENTION

As used herein "to culture 'one' transformed cell" means to initiate culturing from one cell, and also to culture a plurality of cells grown from one cell in the process of culturing.

Transformed cells, comprising genetically engineered cells and hybridoma cells, are cells that are manipulated to constitutively produce a protein and that need not be induced to produce the protein.

Genetically engineered cells refer to those transformed cells into which DNA encoding said protein has been introduced to impart the trait of constitutively producing the desired protein. Genetically engineered cells can be prepared by ligating DNA encoding the desired protein into a suitable expression vector, and introducing the expression vector obtained into a cell by a commonly used method. Such genetically engineered cells include cells in which said DNA has been inserted into the chromosome within the transformed cell and cells in which the DNA has been retained outside of the cell.

Cells suitable for the preparation of genetically engineered cells include all types of host cells and, preferably, eukaryotic cells may be mentioned. As the eukaryotic cells, there can be mentioned animal cells such as mammalian cells, yeast cells, insect cells and the like. As the mammalian cells, preferably there can be mentioned CHO, COS, myeloma cells, BHK (baby hamster kidney), Hela, Vero, and other cells. As the CHO cells, dhfr- CHO (Proc. Natl. Acad. Sci. USA (1980) 77: 4216–4220) that lacks the dhfr gene, CHO K-1 (Proc. Natl. Acad. Sci. USA (1968) 60: 1275), or CHO DG44 (Urlaub, Get al., Cell (1983) 33(2): 405–412) can be preferably used.

Hybridoma cells refer to hybrid cells prepared by fusing cells that constitutively produce the desired protein, such as immunoglobulin-producing cells, with immortalized cells compatible therewith, such as myeloma cells (P3K, YB2/0, U266). In addition, hybridoma cells include immortalized cells, obtained by a means to immortalize cells that produce the desired protein, e.g. by the use of Epstein-Barr virus (EBV). As the cells producing the desired protein that are used to prepare hybridoma cells, there can be used animal cells such as cells from mice, rats, and humans, and the like.

Parent cells refer to cells, before being transformed, of the same strains as the protein-producing cells. As the parent cells, specifically, those cells that were used to prepare protein-producing cells are preferably used. The parent cells of genetically engineered cells are those cells, for example, that were used to introduce DNA encoding the desired protein in the construction of transformed cells and that have not been transformed. The parent cells of hybridoma cells are immortalized cells for use in fusion with immunoglobulin-producing cells.

Selectable marker genes refer to genes that impart the trait that only enables the selective survival of the cells producing the desired protein. According to the present invention, transformed cells that produce protein preferably contain a selectable marker gene. Preferably, parent cells do not contain selectable marker genes.

As the selectable marker genes for use in genetically engineered cells, there can be mentioned aminoglycoside transferase (APH) gene, thymidine kinase (TK) gene, E. coli xanthine guanine phosphoribosyl transferase (HPRT) gene, dihydrofolate reductase (DHFR) gene, and the like. Thus, in order to kill parent cells while keeping the protein-producing transformed cells alive, it is only necessary to culture the cells under a condition under which the cells cannot survive without the expression of the selectable marker gene. Such conditions include the addition of G418, and methotrexate, and the like.

As the selectable marker gene for use in the hybridoma cells, there can be mentioned HPRT and the like. The selectable marker gene may be introduced into the immortalized cells to be subjected to fusion, or the immortalized cells that already contain the selectable marker gene may be fused to the cells that produce the desired protein. The cells containing the selectable marker gene may be cultured under the condition under which the cells cannot survive without the expression of the selectable marker gene. Such conditions include culturing in a hypoxanthine-thymidine-free medium, and the like.

The protein produced by the cells may be any protein that is useful or biologically active. Such proteins include hormones (pituitary hormone-releasing hormones, oxytocins, vasopressins, parathyroid hormone (PTH), parathyroid hormone-related peptides (FTHrP), growth hormone (GH), prolactin, gastrin, secretin, cholecystokinin, insulin, glucagon, calcitonin), enzymes (for example, glucose oxidase), enzyme inhibitors (for example, chymostatin), lymphokines or cytokines (for example, interleukin-1 (IL-1), IL-2, IL-3, IL-4, IL-5, IL-6, IL-7, IL-8, IL-9, IL-10, IL-11, IL-12, IL-13, IL-15, tumor necrosis factor (TNF), interferon-$\alpha$ (IFN$\alpha$), interferon-$\beta$, interferon-$\gamma$, interferon-$\omega$, interferon-$\tau$), hematopoietic factors (for example, erythropoietin (EPO), thromboplastin (TPO), granulocyte colony-stimulating factor (G-CSF), macrophage-stimulating factor (M-CSF), granulocyte macrophage colony-stimulating factor (GM-CSF), stem cell growth factor (SCF), growth factors (for example, vascular epithelial growth factor (VEGF), neuronal growth factor (NGF), fibroblast growth factor (FGF), platelet-derived growth factor (PDGF), transforming growth factor $\beta$(TGF-$\beta$), leukocyte migration inhibitory factor (LIF), ciliary neurotrophic factor (CNTF), oncostatin M (OSM)), immunoglobulins (for example, human antibody, chimeric antibody, humanized antibody, or fragments thereof, Fv, scFv (single chain FV), scFv dimer), and the like. When the cell is a hybridoma cell, the protein is specifically an immunoglobulin.

Culturing or cloning of cells may be carried out using a commonly used method. First, cells that produce the desired protein are suspended into an appropriate culture medium. The medium used may be a commonly used one such as DMEM, MEM, RPMI1640, IMDM, and the like. The medium may be combined with serum supplements such as fetal calf serum (FCS), or with a serum-free medium. The pH of the medium is preferably in the range of about 6–8.

The cells used are preferably in the logarithmic growth phase. When the cells have formed clusters, they can be disentangled by syringing using a syringe of a suitable gauge. The cell suspension obtained may be diluted as appropriate, and plated into a cell culture plate at the rate of one cell/well.

Parent cells may be prepared in a similar manner, and about 1,000–20,000 parent cells, preferably about 3,000–10,000 cells, and more preferably 5,000–10,000 cells are added to a well having one cell of interest. The plate may then be cultured under an appropriate condition. Culturing may generally carried out at about 30–40° C. for about 96–120 hours and, as needed, under an appropriate concentration of carbon dioxide, the replacement, aeration, and shaking of the medium may be carried out.

Since the cells cultured preferably contain a selectable marker gene while the parent cells do not, the parent cells are killed under the condition under which selectable marker gene is expressed leaving the cells of interest alive. The condition under which the selectable marker gene can be expressed may be an addition of methotrexate to the culture medium when the selectable marker gene is dhfr. After the expression of the selectable marker gene, culturing is continued for an appropriate period of time, and then the culture is examined, for example, under a microscope to confirm the formation of colonies of the cells that survived. After the confirmation of colony formation, the culture is transferred to a larger culture vessel as appropriate for an expanded culture. Since the colonies obtained are derived from single cells, the colony formation indicates that the cells have been cloned.

Culturing of the colony obtained is continued and, as appropriate, subjected to subculture and/or expanded culture, and the desired protein produced may be recovered from the culture supernatant or the cells to obtain homogeneous protein. The protein obtained may be purified by combining, as appropriate, column chromatography etc. in a method known to those skilled in the art, and then may be stored and used as desired. Since the protein obtained by the expanded culture of a single cell is homogeneous, the subsequent purification is also easy and a protein with a higher purity can be obtained in a large quantity. It is thus particularly useful in reducing the cost of producing pharmaceuticals. As the column for use in affinity chromatography, affinity column chromatography can be used in which an antibody to the protein has been bound. If the protein is an antibody, a protein A column or a protein G column can be used.

Specifically, as the column that employs protein A, there can be mentioned Hyper D, Sepharose F. F. (Pharmacia), and the like. Ion exchange column chromatography, reverse phase column chromatography, gel filtration column chromatography, etc. can be suitably combined for use (Strategies for Protein Purification and Characterization: A Laboratory Course Manual. Ed. Daniel R. Marshak et al., Cold. Spring Harbor Laboratory Press, 1996). In addition to column chromatography, a crude purification method can be used such as an ultrafiltration membrane method, and an ammonium sulfate method.

Proteins cloned and produced by the single cell cloning of the present invention can be used specifically as pharmaceutical compositions. Though the administration method depends on the activity of proteins, they can be administered systemically or locally via parenteral routes. For example, intravenous, intramuscular, subcutaneous, or intraperitoneal administration can be selected, and the administration method can be selected, as appropriate, depending on the age and disease state of the patient. In addition, depending on the administration route, pharmaceutical compositions may contain pharmaceutically acceptable carriers and/or additives. In particular, pharmaceutically acceptable surfactants, isotonic agents, stabilizers, buffers, solubilizing agents, analgesics, sulfer-containing reductants, and antioxidants may be added.

The present invention will now be explained with reference to the following examples, but it should be noted that they do not limit the scope of the invention in any way.

EXAMPLE 1

Co-Culturing with Parent Cells

CHO DG44 cells, the parent cells, were passaged and cultured in the HO-S-SPM II(DPM) medium (manufactured by GIBCO-BRL) supplemented with a 1% HT supplement (manufactured by GIBCO-BRL), and the CHO DG44 cells at the logarithmic growth phase were used. CHO DG44 cells into which a gene encoding humanized anti-HM1.24 antibody has been integrated were prepared by the method described in International Patent Publication WO98/14580. The humanized anti-HM1.24 antibody-producing CHO cells thus obtained (an expression vector HEF-RVHs-AHM-g$\gamma$1. (FERM BP6127) for humanized anti-HM1.24 antibody H chain and an expression vector HEF-RVLa-AHM-g$\kappa$ (FERM BP5645) for humanized anti-HM1.24 antibody L chain were used to simultaneously transform the CHO cells) were used as the transformed cells.

Humanized anti-HM1.24 antibody-producing CHO cells were prepared in a method similar to that in International Patent Publication WO98/14580. The humanized anti-HM1.24 antibody-producing CHO cells were subcultured in a CD-CHO medium (manufactured by GIBCO-BRL) supplemented with 640 μg/mL G418 (manufactured by GIBCO-BRL), 50 nmol/L MTX and 8 mmol/L L-glutamine prior to use. Since these cell had slightly formed cell clusters, syringing treatment with a 23 G needle was performed to disentangle the cells.

After the humanized anti-HM1.24 antibody-producing CHO cells were washed in a medium used for subculturing, the cell concentration was adjusted to one cell/well using said medium to obtain 250 ml of a cell suspension (20 cells/ml). The cell concentration of the parent cells, CHO DG44 cells, were adjusted using the same medium to 100 cells/well, 1,000 cells/well, and 10,000 cells/well to obtain 150 ml of a cell suspension ($1 \times 10^3$ cells/ml, $1 \times 10^4$ cells/ml, $1 \times 10^5$ cells/ml).

0.05 ml of the suspension of humanized anti-HM1.24 antibody-producing CHO cells and 0.1 ml each of the CHO DG44 cell suspensions were plated into a 96-well plate. Thus, each well contained one humanized anti-HM1.24 antibody-producing CHO cell. Similarly, fifteen 96-well plates were prepared for a total of 1440 samples for each suspension.

After culturing in a 5% CO2 incubator at 37° C. for 14 days, they were examined under a microscope. From the wells in which colony formation was confirmed, cells were collected and were subjected to expanded culture to a 24-well plate (1 ml) using the same culture medium to secure stable growth of the cells. The number of wells for which colonies of the cells were confirmed is shown in Table 1.

TABLE 1

Cloning result of the parent strain-added assay

| Number of cells for parent strain | Number of colonies formed |
|---|---|
| (a) | |
| 100 cells/well | 0 |
| 1,000 cells/well | 6 |
| 10,000 cells/well | 58 |
| Total | 64 |
| (b) | |
| 1,000 cells/well | 6 |
| 10,000 cells/well | 30 |
| Total | 36 |

In Table 1, (a) indicates the number of colonies selected during microscopic examination (i.e. the number of colonies subcultured to 24-well) (day 14), and (b) indicates the number of colonies expanded from 24-well plates to 6-well plates.

No colonies of the humanized anti-HM1.24 antibody-producing CHO cells were formed in the wells co-cultured with 100 cells/well of the CHO DG44 cells, whereas in the wells co-cultured with 1,000 cells/well or 10,000 cells/well of the CHO DG44 cells, 6 and 30 colonies, respectively, were confirmed.

Thus, this suggests that by co-culturing with 1,000 cells/well or 10,000 cells/well of parent cells, even one cell/well concentration of the transformed cell can be grown to obtain single clones, and a method using co-culture with parent cells enabled single cell cloning that had previously been considered impossible. Colonies that exhibited stable growth at the expanded culture using 24-well plates were cultured in the presence of 640 μg/ml of G418 and 50 nM MTX thereby to obtain homogenous humanized anti-HM1.24 antibody-producing CHO cells.

EXAMPLE 2

Expanded Culture $1 \times 10^5$ cells of the humanized anti-HM1.24 antibody-producing CHO cells that were subjected to expanded culture were cultured for 11 days in a Primatone 10 g/l added CHO-S-SFM II medium (6 liters×three tanks) under a condition of pH 7.2, DO60% air-saturated, and 60 rpm. The culture supernatants from the three tanks were combined, filtered by Sartobran PH Capsule (Sartorius), loaded to a rProtein A FF column (Pharmacia), washed with 1M NaCl/10 mM citrate phosphate buffer, pH 7.5, and 10 mM citrate phosphate buffer, pH 7.5, and then eluted with 2.5 mM HCl, pH 2.7.

In order to remove endotoxins, Kurimover (Kurita Kogyo) was directly fed into the Protein A-elution fraction obtained, which was stirred at 4–10° C. for 6 hours. By filtering with a cellulose acetate filter 0.2 μm (Corning), 2.65 ml of a humanized anti-HM1.24 antibody solution was obtained. The humanized anti-HM1.24 antibody obtained was confirmed to be almost homogeneous by reverse phase HPLC analysis.

EXAMPLE 3

Using humanized anti-HM1.24 antibody-producing CHO cells and humanized anti-PHTrP antibody-producing CHO cells, single cell cloning by co-culture with the parent cells, CHO DG44 cells, and single cell cloning by other methods (the conditioned medium method, the serum addition method, and the cell lysate method) were compared.

The CHO DG44 cells into which a gene encoding humanized anti-PTHrP antibody had been integrated were prepared by the method described in International Patent Publication WO 98/13388. The thus obtained humanized anti-PTHrP antibody-producing CHO cells (an expression vector hMBClHcDNA/pUC19 (FERM BP-5629) for humanized anti-PTHrP antibody H chain and an expression vector hMBClLq λcDNA/pUC19 (FERM BP-5630) for humanized anti-PTHrP antibody L chain were used to simultaneously transform the CHO cells) were used as the transformed cells. Furthermore, GIBCO CHO-S-SFMII-modified/CD-CHO medium (the half medium) was used as a fresh medium for humanized anti-HM1.24 antibody-producing CHO cells, and GIBCO CHO-S-SFMII medium was used as a fresh medium for humanized anti-PTHrP antibody-producing CHO cells.

(1) Method of Co-Culturing with Parent Cells

The humanized anti-HM1.24 antibody-producing CHO cells or the humanized anti-PTHrP antibody-producing CHO cells on day 1 of culture were diluted in a fresh medium so that 0.2 ml each thereof contains one cell, to which 5,000,000 parent cells, DG44CHO cells, were added and suspended. The cell suspension was inoculated to five 96-well plates at 0.2 ml/well.

(2) Conditioned Medium (CM) Method

The supernatant after centrifuging the transformed cell culture on day 1 of culture was filtered by a 0.2 μm filter. To the filtrate was added the suspension at an amount equivalent to 500 transformed cells on day 1 of culture to make a final volume of 100 ml. The cell suspension was inoculated to five 96-well plates at 0.2 ml/well. In a method employing the culture liquid on day 3 of culture, the centrifugation supernatant of the transformed cell culture liquid on day 3 of culture was used in a similar manner.

(3) Serum Addition Method

The transformed cell culture liquid on day 1 of culture was diluted in a fresh medium to obtain one cell/200 µl. To 90 ml of this diluent, 10 ml of FBS (Fetal Bovine Serum I.S.C at #3000 Lot #300050933) was added and suspended to five 96-well plates at 0.2 ml/well.

(4) Cell Lysate Addition Method

The transformed cell culture liquid on day 1 of culture was diluted in a fresh medium to obtain one cell/200 µl. The precipitate of the cell lysate was suspended to this diluent, which was plated to five 96-well plates at 0.2 ml/well. The above cell lysate was prepared as follows. Thus, after 5,000,000 cells of the parent strain on day 3 of culture were centrifuged, it was suspended in 10 ml of sterile water. After freezing at −80° C. and repeating the thawing twice at 37° C., it was centrifuged at 3500 rpm for 60 minutes. The precipitate was rinsed in 10 ml of sterile water, and centrifuged again at 3500 rpm for 60 minutes to prepare a cell lysate.

Result

The appearance of colonies of the humanized anti-HM1.24 antibody-producing CHO cells and the humanized anti-PTHrP antibody-producing CHO cells for each method was observed on day 20 and 21 after plating, and the rate of colony appearance per plate is shown in Table 2. As a result, single cell cloning was possible for both of the cells by co-culture with the cell of the parent strain.

When single cell cloning was impossible with other methods as observed for humanized anti-HM1.24 antibody, single cell cloning by co-culturing with the cells of the parent strain proved to be effective. When one, three, 10, 30, and 100 cells/well were plated only for the transformed cells as the control, colonies were formed for any of the transformed cells when 30 or 100 cells were plated, but no colonies were observed when 10 or fewer of the transformed cells were plated.

TABLE 2

Rate of colony appearance in each cloning method

| Cloning method | Number of colonies appeared (colonies/plate) |
| --- | --- |
| (A) Humanized anti-PTHrP antibody (day 20) | |
| Co-culturing with the parent strain | 23.0 |
| Conditioned medium method (day 1) | 10.6 |
| Conditioned medium method (day 3) | 6.6 |
| Serum addition method | 27.2 |
| Cell lysate addition method | 4.6 |
| (B) Humanized anti-HM1.24 antibody (day 21) | |
| Co-culturing with the parent strain | 36.4 |
| Conditioned medium method (day 1) | 0.0 |
| Conditioned medium method (day 3) | 0.0 |
| Serum addition method | 0.0 |
| Cell lysate addition method | 0.2 |

INDUSTRIAL APPLICABILITY

The present invention enabled culturing or cloning of one cell that produces a desired protein.

What is claimed is:

1. A method for culturing a protein-producing cell comprising:
   (1) preparing transformed cells that can constitutively produce said protein;
   (2) isolating a single transformed cell from the cells prepared in (1); and
   (3) co-culturing the single transformed cell isolated in (2) with parent cells;
   wherein the transformed cells are genetically engineered cells or hybridoma cells;
   wherein if the transformed cells are genetically engineered cells, the parent cells are cells before being transformed, of the same strain, and if the transformed cells are hybridoma cells, the parent cells are immortalized cells used to prepare the hybridoma.

2. A method for cloning a protein-producing cell comprising
   (1) preparing transformed cells that can constitutively produce said protein;
   (2) isolating a single transformed cell from the cells prepared in (1); and
   (3) co-culturing the single transformed cell isolated in (2) with parent cells;
   wherein the transformed cells are genetically engineered cells or hybridoma cells;
   wherein if the transformed cells are genetically engineered cells, the parent cells are cells before being transformed, of the same strain, and if the transformed cells are hybridoma cells, the parent cells are immortalized cells used to prepare the hybridoma.

3. The method according to claim 1 or 2, wherein said hybridoma cell or the genetically engineered cell is a cell that contains a selectable marker gene.

4. The method according to claim 1 or 2, wherein the protein produced by the genetically engineered cell is a biologically active substance.

5. The method according to claim 4, wherein the biologically active substance is a hormone, an enzyme, a lymphokine, a cytokine, a growth factor, or a transcription factor, or a derivative thereof.

6. The method according to claim 1 or 2, wherein the protein produced by the hybridoma cell or the genetically engineered cell is an immunoglobulin or a derivative of an immunoglobulin.

7. The method according to claim 6, wherein the immunoglobulin is a mouse antibody, a rat antibody, a chimeric antibody, a humanized antibody, or a human antibody.

8. The method according to claim 7 wherein the humanized antibody is humanized anti-HM1.24 antibody.

9. The method according to claim 6, wherein the derivative of an immunoglobulin is Fab, F(ab')2, or a single chain Fv.

10. The method according to claim 1 or 2, wherein the transformed cell is a mammalian cell, a yeast cell, or an insect cell.

11. The method according to claim 10, wherein the mammalian cell is a CHO cell.

12. The method according to claim 1 or 2, wherein the number of parent cells to be co-cultured is 1,000 to 10,000.

13. A method of producing protein, comprising:
   (1) preparing transformed cells that can constitutively produce said protein;
   (2) isolating a single transformed cell from the cells of (1);
   (3) co-culturing the single cell from (2) with parent cells of the transformed cell to select a transformed cell having the desired property;

(4) subjecting the transformed cell selected in (3) to at least one of a subculture and an expanded culture; and (5) harvesting said protein from culture supernatant or the cell;

wherein the transformed cells are genetically engineered cells or hybridoma cells;

wherein if the transformed cells are genetically engineered cells, the parent cells are cells before being transformed, of the same strain, and if the transformed cells are hybridoma cells, the parent cells are immortalized cells used to prepare the hybridoma.

* * * * *